United States Patent [19]

Thiel

[11] Patent Number: 5,002,956
[45] Date of Patent: Mar. 26, 1991

[54] USE OF HETEROCYCLIC COMPOUNDS FOR IONTOPHORETIC TREATMENT

[76] Inventor: Karl H. Thiel, Mandrystrasse 10, D-7100 Heilbronn, Fed. Rep. of Germany

[21] Appl. No.: 326,997

[22] Filed: Mar. 22, 1989

[30] Foreign Application Priority Data

Mar. 23, 1988 [DE] Fed. Rep. of Germany ....... 3809814
Jun. 10, 1988 [DE] Fed. Rep. of Germany ....... 3819842

[51] Int. Cl.$^5$ ..................... A61K 31/44; A61K 31/47; A61K 31/33; A61N 1/30
[52] U.S. Cl. ................................. 514/297; 514/311; 514/313; 514/183
[58] Field of Search ........................... 604/20, 21, 183; 514/187, 188, 297, 311, 313

[56] References Cited

U.S. PATENT DOCUMENTS 4,314,061 2/1982 Murdock et al. ..................... 544/80
4,824,676 4/1989 Bodor .................................. 424/449

OTHER PUBLICATIONS

A Search for Anti Tumor Compounds. Hrabowska et al., Chem. Abst. #72040r 85, 1976.
Study on Drugs for Cancer Therapy. Synthesizing 9-Aminoacidine Compounds, Zhang et al., Chem. Abst. #239185w, 93, 1980.
Inhibition of t RNA Nucleotidyl Transferen–Girgenti et al., Chem. Abst. #117676a, 84, 1976.
The Effect of Colchicine Applied by Iontophon, Levkut et al., Chem. Abst. #87713e, 108, 1988.
Studies on Surgical Adjuvant–. Akao. Chem. Abst. 2078779.97, 1982.

Primary Examiner—Merrell C. Cashion, Jr.
Assistant Examiner—G. S. Kishore
Attorney, Agent, or Firm—Dressler, Goldsmith, Shore, Sutker & Milnamow, Ltd.

[57] ABSTRACT

What is disclosed is the use of dissociable heterocycle compounds from the group including aminoacridine, aminocholine and aminopyridine as well as their derivatives substituted on the basic structure, which are present in tautomeric diimine form, for the selective iontophoretic treatment or for production of a pharmaceutical for iontophoretic treatment and relapse prophylaxis of bladder cancer as well as for iontophoretic treatment of malignant skin and mucus membrane tumors.

It is further disclosed and proven that the antineoplastic effect observed with use of the above compositions in animal experiments and in clinical treatment is selective and healthy tissue is not damaged.

The common denominator for the characteristic and proven antineoplastic selective effect of the three classes of materials is the tautomeric diimine form.

As a pre- and/or post-treatment medium with the treatment of bladder cancer, preferably a lubricant, anesthetic and prophylactic medium is used, which includes
(a) a nonionic, water miscible lubricant with an electric conductivity lower than 2 mS/cm and a viscosity (at 25° C.) in the range of 50 to 2000 mPa.s, and
(b) a local, nonionic mucus membrane anesthetic which does not penetrate into the bloodstream, in which the mixture of (a) and (b) has a pH level between approximately 5 and 7.5, preferably between 6.5 and 6.8.

17 Claims, 1 Drawing Sheet

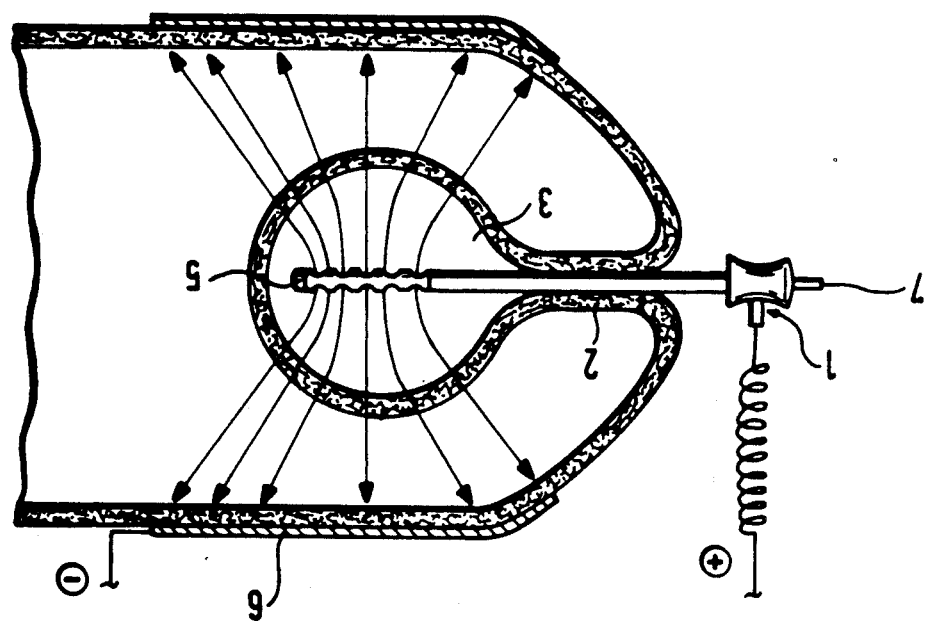

USE OF HETEROCYCLIC COMPOUNDS FOR IONTOPHORETIC TREATMENT

DESCRIPTION

The invention relates to the use of certain heterocyclic compounds for iontophoretic treatment or for the production of pharmaceuticals for iontophoretic treatment of malignant tumors as well as a lubricant or parting compound, anesthetic and prophylactic for introduction and use during this treatment.

It is already known that certain heterocyclic compounds, i.e. acridine, quinoline and pyridine derivatives with a nitrogen atom in a heterocyclic ring and at least one amino group remaining separate from the ring structure, which with the nitrogen atom in the ring structure can develop a tautomeric diimine structure, represent mitotic poisons (cf. Lettré H.: Uber Mitosegifte, Ergebnisse der Physiologie, /On Mitotic Poisons, Physiology Publications/, 46, 379–452 (1950)).

Some of these heterocyclic compounds with two or more condensed aromatic ring structures have the capacity to and may become incorporated in the double helix of the deoxyribonucleic acid (DNA) of bacteria or tissue cells in such a manner that both the replication and the biochemical transcription can no longer elapse in an orderly manner. These molecules are designated as intercalaries (cf. D. Schmael, Arzneimittelforschung/-Pharmaceutical Digest/, 21st supplement, 3d edition (1981), p. 424). The biological interaction of these heterocyclic compounds, especially the acridine compounds, probably is based on an intercalation with the DNA by placement or implantation between the base pair layers, which is conditioned by the flat structure of these heterocyclic compounds. Guanine-cytosine-base pairs are thus preferred, and the formation of a complex with DNA and a repair enzyme probably occurs. The activity of the polymer is reduced, and the DNA cannot be uncased. Furthermore the DNA helix is broken down into single and double strands with consecutive DNA-protein bonds.

European Patent Application 35 862-A2 introduces the use of 4'-(9-amino-acridinemethane sulfone-m-anisidide as antineoplastic agent. In this case however it concerns something other than an amino-acridine, which is present in a tautomeric diimino form. The compound is extremely toxic, and thus is scarcely usable. With certain solid tumors its effect was only so slight that it was not used at all in one clinical-therapeutic program. In particular, it was not used for the treatment of bladder carcinomas but rather found its preferred use for treatment of leukemia. Local use is inadvisable because of its tissue-destroying effect.

Swiss Patent 647 677 relates to a pharmaceutical mixture containing 4'-(9-acridinyl amine)-methane sulfone-m-anisidide in a mixture with lactic acid in mole ratio of 1.5:1to 4:1. therefore in this case it has to do with the same acridine derivative as is described in European Patent 00 35 862A2, and the water solubility of the effective substance is to be heightened by its salt formation with lactic acid, so that it is suitable for the intravenous administration. Oral administration is also possible. In this case it is considered as a systemic pharmaceutical.

THE MERCK INDEX 1983 cites acriflavine, proflavine and streptonigrine, which are cited as anti-infectant or antiseptically effective pharmaceuticals. Streptonigrine was also cited as an antineoplastic agent. However no reference is found to the use of these compounds for the treatment of solid tumors, especially for carcinomas of the bladder.

It is known from the literature from CA 84:117676a that the t-RNA-nucleotidyl-transferase of Ehrlich's tumor cells in inhibited by proflavine sulfate and ethidene bromide. In these experiments, however, it has to do with only experimental cells to be used as mitotic inhibitors, so that from these results it could not be predicted how the proflavine would behave with solid tumors, especially in the case of carcinomas of the bladder.

From "Folia Veternnavia", 31.1 (1987), pages 135 to 140 (CA 108: 87713e) it is known that colchicine can be used for iontophoretic treatment of tumors which had been induced by ASV (Avian Sarcoma Virus). Chickens were treated. In the case of colchicine however the involvement was not with a heterocyclic compound with amino functions, which could be present in a tautomeric diimine form Colchicine is a strong mitotic poison, which is why it has not been used in human cancer therapy until this time.

Finally, in CA 97: 207877 g, the literature describes the iontophoretic treatment of colon-rectal tumors with the use of a double balloon catheter, in which 5-fluoruracil or neocarcinostatin is applied intraluminally.

Neither of these compounds falls into the group of amino substituted heterocyclic compounds which may be present in a tautomeric diimine form.

It has now been discovered that heterocyclic compounds of the type described by the aforementioned Lettre, in the case of malignant tumors, do not display their antineoplastic effect until they are introduced into the tumor tissue in an iontophoretic process or until, following conventional local application, for instance by injection, direct current (iontophoresis) is applied.

The antineoplastic effect is selective, and healthy tissue is not damaged.

The object of the invention is thus the use of dissociable heterocyclic compounds from the group including amino acridine, amino choline and amino pyridine as well as their derivatives substituted on the basic structure, which are present in a tautomeric diimine form, for the iontophoretic treatment or for the manufacture of a pharmaceutical for the iontophoretic treatment and relapse or recidivism prophylaxis of bladder cancer as well as for the iontophoretic treatment of malignant skin and mucus membrane tumors.

The basic problem to be resolved according to the invention is explained hereinafter in the example concerning the bladder carcinoma.

A polychronotopic neoplastic of the entire bladder mucus membrane is the basis of the bladder carcinoma. Each of its segments can in timed progression be the starting point for tumor formation. In most cases at the time of the first diagnosis and therapy cystoscopically diagnosable tumor zones are associated with the generative tumor cells which are not yet macroscopically visible. This fact explains the extremely high recidivism of carcinomas of the bladder. With these subsequent tumors then it is not a matter of traditional "recidivism" but rather of new manifestations in the area of the ubiquitous and potentially infected mucus membrane, being generated from those tumor centers which are not detected diagnostically and are not subjected to therapy. This particular configuration of the tumor formation constitutes the real diagnostic, therapeutic and prognostic dilemma of bladder cancer disease.

To escape this dilemma, practitioners have tried to implement local chemotherapy with certain antitumor agents for the regression of residual tumors and for prophylaxis against recidivism following removal of tumors which are found, for instance by transurethral electro-resectioning. This occurs when this material is introduced in aqueous solutions through a catherter into the bladder and is left there for approximately two hours.

However this local chemotherapy has not been particularly successful in the matter of ridding the body of residual tumors or for prophylaxis against recidivism, since the bladder is not a resorptive organ. The top surface cell layer of the mucus membrane represents a membrane through which ionic substances cannot pass. Nonionic compounds may cross the membrane under certain conditions, which is why the non-ionic antitumor agents are the preparations used for local chemotherapy. They must have a molecular weight above 200, since substances with lower molecular weight are picked up by the blood vessels immediately after passing through the membrane and are carried away. The lower the molecular weight, the more superficial is the antitumor effect within the bladder wall, and the closer in effect is this local chemotherapy to a systemic chemotherapy in relation to side effects. Any local chemotherapy of the bladder therefore has the same drawback as any systemic chemotherapy. These pharmaceuticals are not selective, cannot differentiate between healthy and diseased cells, damage the mucus membrane, cause various subjective ailments and can in turn lead to cancerous tumors.

The use of the aforementioned heterocyclic compounds according to the invention, which are present in dissociable form, in other words in solution in ionic form, for iontophoretic tumor treatment or for the manufacture of pharmaceuticals for iontophoretic tumor treatment now discloses the possibility of a conservative, protective treatment, in other words a highly concentrated localized antineoplastic treatment in all bladder layers without systemic side effects and without causing tumor regeneration and with simultaneous prophylaxis against recidivism.

"Iontophoresis" in the usage of the invention is intended to mean the diffusion of the heterocyclic compounds which are present in dissociated form, in other words in ionic form, through the skin and the mucus membrane into the tumor under the influence of direct current. Iontophoresis, however, is a very complex procedure, in which are also invested other phenomena, such as electrophoresis, electroosmosis, electrolysis and diffusion. The direct current causes thorough and rapid distribution of the heterocyclic compound in the tumor tissue. Furthermore with iontophoresis there is, probably a current effect tending to neutralize the electric double layers of the cell membranes or respectively the cell nucleus membranes, whereby the blocking effect of these membranes relative to the heterocyclic compounds present in ionized form is nullified. Another special flow effect is present in that the heterocyclic compound in the tumor cells or in the tumor cell nucleus when under the effect of direct current causes an inhibition of cell division with subsequent cell decline (tumor regression). This effect is selectively directed onto the tumor cells and does not damage healthy body tissue.

Either single or multi-nucleus heterocyclic compounds could be used according to the invention, which in addition to the nitrogen atom in the heterocyclic ring include another one or more amino groups. Single nucleus heterocyclic compounds may be for instance 2- and 4-amino pyridines, which can be present as opposed to 3-amino pyridine in the tautomeric diimine form. Examples of two-nucleus heterocyclic compounds, which can be present in tautomeric form, are 4- and 7-amino quinoline. These compounds are present in the form of salts, in which the cation forms the effective portion of the heterocyclic compound.

The heterocyclic compound is preferably present as a mono- or di-chloride, -sulfate, -lactate, or -acetate, and the preferred heterocyclic compound to be used is profavine monohydrochloride, which is defined chemically as 3,6-diaminoacridine hydrochloride and which has the following general formula:

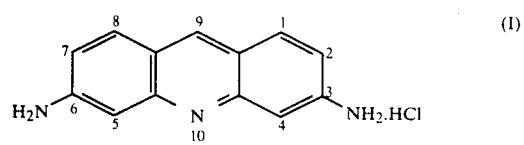

The tautomeric diimine form can be represented by the following general formula:

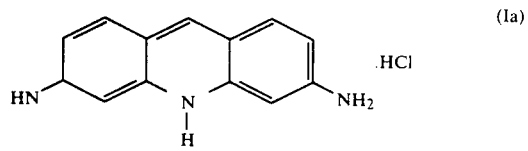

Another example of a heterocyclic compound used according to the invention is trypaflavine or acriflavinium chloride (international name used for the mixture of hydrochloride of 3,6-diamino-10-methylacridinium chloride (cf. the following general formula):

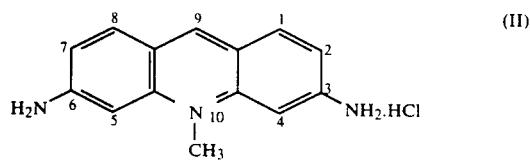

and 3,6-diaminoacridine.

The heterocyclic compounds used according to the invention could be substituted on the basic structure, in other words both on the nitrogen atom in the heterocyclic ring and on the carbon atom on the ring by substituents such as halogen, alkyl or alkoxy groups (especially with 1 to 4 carbon atoms), aryl groups, alkaryl groups and aralkyl groups (especially in which the aryl groups represent a phenyl group).

The heterocyclic compounds used according to the invention in the iontophoresis act on the tumor cells selectively. In all probability this occurs because of the difference between the membrane behavior of tumor cells and healthy cells, especially in the nuclei and mitochondria, since it leads to an accumulation of the heterocyclic compounds on the DNA under the influence of the electric current only in the tumor cell as manifestation of an irreparable cell decline only in the tumor cells.

According to one preferred embodiment the heterocyclic compounds used in the invention are present in mixture with dimethyl sulfoxide (DMSO) in aqueous solution. In connection with the iontophoresis, the DMSO causes a threefold increase of the volume of transported heterocyclic compound, which is the active component, in comparison with a bladder instillation without DMSO. DMSO alone however is not in the position to make this surface cell layer working as membrane of the bladder mucus membrane permeable for ionic substances as are the relevant heterocyclic compounds, nor make possible a stronger concentration of the heterocyclic compounds in the bladder wall. On the other hand the DMSO improves the overall distribution of the heterocyclic compounds in the tissue, which is of great importance for the antineoplastic detection all tumor cells.

In the treatment of carcinomas of the bladder, DMSO also has a local analgesic and spasmolytic effect, and with the current densities which are being applied iontophoreses are possible for a longer time period.

Heterocyclic compounds in aqueous solution used according to the invention usually are present in a concentration of 0.05 g/l up to the limits of solubility, preferably up to 5 g/l. Dimethyl sulfoxide is present preferably in aqueous solution in a concentration of 20 to 300 g/l.

One preferred prescription contains proflavine monohydrochloride in a concentration of 0.05 to 5 g/l and DMSO in a concentration of 20 to 300 g/l. The prescription particularly contains 1 g/l · proflavine-monohydrochloride and 150 g/l dimethyl sulfoxide. With use of such a prescription, the iontophoresis in any one session can be extended by ½ hour and longer.

The iontophoretic treatment is preferably applied with a direct current, and the current densities applied to the body surfaces or the tumors are not over 0.5 mA/cm$^2$. "Direct current" also includes pulsing or intermittent direct currents as well as certain types of alternating current, in which one half period has a greater amplitude than the other half period or respectively in which the integral surface is greater below one half period than below the other half period. The iontophoresis leads to a migration of the heterocyclic compounds which are present as cations in the body tissues and in the tumor cells. In the further developement—as already described—following the aggressive penetration of the membrane structures, the next primary function is an interaction involving the nucleus and mitochondria which takes place as an interaction of the heterocyclic compounds with the DNA of the tumor cells, but this fails to occur with healthy tissues. This phenomenon constitutes the selective antineoplastic effect of the heterocyclic compounds during iontophoresis.

During treatment of carcinomas of the bladder the medication is preferably introduced with the aid of a positive electrode 1 of tubular configuration, as is shown in the drawing, through the urethra 2 into the bladder 3. The positive electrode is insulated in the area of the urethra, in the area of the bladder is provided with openings 4, and at the distal end 5 is provided with a cap of insulating material. The negative outside electrode in the form of a sort of reinforced belt is indicated as 6 in the drawing. The arrows indicate the direction of flow or respectively of material transport from the inside of the bladder into the bladder wall and to the outside negative electrode. The bladder instillation, which is introduced at 7, contains a mixture of distilled water, heterocyclic compound (particularly proflavine-monohydrochloride) and DMSO in the aforementioned range of concentration.

The bladder is an ideal receiver organ for iontophoresis, since it is capable of holding a solution of an electrolyte, in other words a solution containing the heterocyclic solution in ionic form, and allows for the desired damming up and penetration into the bladder wall. Theoretically the volume of heterocyclic compound which is transported from the instillation in the bladder into the bladder wall is the product of time multiplied by the current intensity; in practice however it must also be considered that during the iontophoretic treatment with the urine, impurity ions may get into the instillation, where they compete with the heterocyclic compound ions which are to be transported for application to the diseased area. Therefore the treatment solution which is to be used must be free of impurity ions and have a sufficiently high heterocyclic compound concentration to prevent the material transport from occurring preponderantly in connection with the impurity ions.

After a treatment time of 30 minutes, the dammed up material can be detected in high concentrations in all three bladder wall layers, which until this time could not be attained without use of intravascular iontophoresis.

The proflavine (in cation form) which is preferred according to the invention is characterized by its good tissue compatibility. In therapeutic doses (1 g/l), proflavine does not irritate the tissue and also does not cause any allergic reaction. It is effective whatever the pH value and is characterized by a good chemical stability. An extremely high bacteriostatic and bactericidal effect occurs in solutions of even the lowest proflavine concentration.

During iontophoretic treatment of bladder cancer it has been established that complications sometimes arose during introduction of electrode 1 thorough the urethra into the bladder, when no lubricant was used, Lubricants are already used for the diagnosis and during the therapy of bladder diseases (bladder examination by means of a speculum or electrosections), in order to be able to introduce the instruments required for this purpose into the urethra without added complication. These lubricants are of various compositions (gels, emulsions) and most of them are mixed with a mucus anesthetic, so as to accomplish introduction of the instrument largely without pain.

In the procedures of electrical operations in the bladder accomplished for instance through the urethra, using high frequency currents and an instrument which has a metal shaft, lubricants with high conducting capacity (about 7 mS/cm) are used, while with devices with an insulated shaft (the shaft in this case lying within the urethra), lubricants with lower conducting capacity (about 1 to 2 mS/cm) are used. In this case it is possible to avoid great pain in the urethra, painful electric urethral irritations and damages (burning, strictures) caused by deviating currents or current leakage.

When the electrode 1 according to the invention is introduced through the urethra into the bladder, with the aid of an ion conductive commercial lubricant mixed with a local anesthetic, then the following occurs:

(a) With application of the electrode through the urethra into the bladder, a portion of the lubricant present in the electrolyte mixture also gets into the bladder. There, embodied in the form of the aforementioned impurity ions, it competes with the ionic heterocyclic compound, of which the conveyance into the bladder wall and hence into the tumor and of which the antineoplastic effect are thus considerably lessened and are thus respectively weaker.

(b) With even a slight spasm of the bladder a small volume of liquid can penetrate into the urethra from the therapeutic bladder instillation of the dissociable heterocyclic compound while the iontophoresis is being carried out. It is ionically conductive and in this case, combined with the likewise conductive lubricant, directly exposes the sensitive urethral mucus membrane to the current. The more irregular the current distribution (different thicknesses of lubricant layers), the further are the current densities beyond the tolerance limits, measured an any one point, whereby damages occur to the mucus membrane until it reaches colliquative necrosis. The immediate results still under iontophoresis can be, depending on the level of anesthesia, queasy sensations or pain. This can lead to painful bladder contraction, which diminish the bladder capacity and allow the therapeutic bladder instillation to drain away alongside the probe and subsequently bring about premature termination of the treatment. If on the other hand the anesthesia is sufficient, the just described symptoms do not occur, and the iontophoresis is completed in good order. After several hour up to one day however the aliment symptoms set in quite acutely and markedly (painful pollakiruia, or unduly frequent passage of urine, sharp burning in the urethra and so forth), which can obviate or preclude the second session within a treatment cycle which must necessarily be carried out within the interval of seven days. The series of symptoms is for the most part therapy resistant and can last in declining intensity for as long as 4 weeks. It intensifies from cycle to cycle, whereupon further iontophoretic treatment and thus the total therapy results are brought into question.

This problem arises especially with patients in whom the bladder is badly damaged by long and conventional treatment measures (electrosectioning, local use of antitumor agents) and when the bladder is found in a supersensitive state (inclined to spasms).

So as to avoid the aforementioned problems and to facilitate an effective and painless iontophoretic treatment of cancer of the bladder, then preferably a lubricant, anesthetic and protective agent is used, which is characterized in that it incorporates the following:

(a) a nonionic lubricant which is water miscible, with an electric conductivity below 2 mS/cm and a viscosity (at 25° C.) in the range of 50 to 2000 mPa.s, and
(b) a local, nonionic anesthetic for the mucus membrane, which does not penetrate into the blood stream, and the mixture of (a) and (b) is at a pH level between 5 and 7.5.

The medium according to the invention is suitably compatible because of its pH level of 5 to 7.5, preferably 6.5 to 6.8. It may not exceed the given electric conductivity, and its conductivity is preferably lower than 1, more preferably lower than 0.5 mS/cm; it must also display sufficient viscosity, so that a continuous film remains between the wall of the urethra and the inserted electrode.

It s viscosity (at 25° C.) lies in the range of 100 to 1500 mPa.s.

In its function as pre-treatment medium, the medium according to the invention allows for painless and non-traumatic introduction of the electrode through the urethra and into the bladder at one pass while it also protects the urethra from damage from electric leakage currents during the iontophoretic treatment. Also, if there is unintended discharge of an excess quantity of the medium, no impurity ions are leaked into the therapeutic bladder instillation (in other words of the heterocyclic compound present in ionic form) and thus the arrangement prevents any diminishment of the effectiveness of the transport or respectively of the antineoplastic effect of the heterocyclic compound.

In its function as post-treatment medium, in other words when it is applied following termination of the iontophoresis through the tubular electrode still lying in the bladder, the medium according to the invention causes surface anesthesia of the entire bladder mucus membrane and thus precludes the occurrence of bladder spasms which may otherwise occur following the treatment, causing constrictive pollakiuria and pain, which could make the execution of further treatment within a set time period on only a few days impossible, even though it is deemed necessary.

Use of a traditional local anesthetic such as lidocain in this case would be contraindicated, because such a medication would be very rapidly resorbed through the bladder wall and would become systemic, effecting the entire body. The quantities required to be effective on the large bladder surface would be a lethally dangerous dose.

The lubricant (a) could be preferably a polyol or a polyol derivative, which are water miscible, for instance diethylene glycol, triethylene glycol and more highly poymerized polyethylene glycols. Also triols and more highly polymerized polyols such as those derivative which are etherized may be used. Glycerine is especially preferred.

The local anesthetic, which is likewise a local tissue-compatible and nonionic substance, is preferably a polyethylene glycol ether with a molecular weight of greater than or equal to 450. The local anesthetic is represented by a polyethylene glycol monododecyl ether of the following formula:

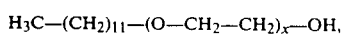

$$H_3C-(CH_2)_{11}-(O-CH_2-CH_2)_x-OH,$$

in which x represents a number between 6 and 12. This compound is cited more briefly with the internationally accepted short name polidocanol.

The lubricant, anesthetic and prophylactic according to the invention is especially characterized in that the weight ratio between lubricant (a) and local anesthetic (b) is approximately 10 to 200:1, preferably approximately 15 to 100:1, and most preferably 20:1.

The medium according to the invention preferably is carried in the form of a solution of polidocanol in glycerine of about 0.5 to 7% by weight, especially of about 5% by weight, The invention will be clarified in more detail in the following examples.

EXAMPLE 1

Intravascular Iontophoresis with Proflavine-Monohydrochloride

A bladder instillation was undertaken with 200 ml of a 0.1% proflavine-monohydrochloride solution, and no remarkable subjective and objective local symptoms of irritation occurred. The treatment lasted for 30 minutes, the current amperage which was used was 50 mA, whence analytically, in the area of the entire bladder wall (surface), a current density of 0.3 mA/cm$^2$ was obtained.

Following the treatment, the following concentrations of proflavinemonohydrochloride solution were identified in the three bladder layers:

(I) mucus membrane: 5.20 μg/g
(II) muscularis: 13.80 μg/g
(III) perivascular tissue 2.10 μg/g.

For comparison, a corresponding bladder instillation but without iontophoresis was undertaken. In this case no medication penetrated into the bladder wall, which was determined by excision of a specimen and testing by means of liquid chromatography.

The iontophoretically attained proflavine-tissue levels on the one hand unmistakeably indicate that the substance does not immediately enter the vascular system following its passage through the cell layer of the bladder mucus membrane which is otherwise not superficially penetrable by ionized compounds and is working as a membrane, and is transported away, but rather that is distributed throughout the entire bladder wall and on the other hand, that the maximum portion of the proflavine concentration remains in the muscual (layer II). That is especially important for treatment of the wall-infiltrating forms of bladder carcinomas.

EXAMPLE 2

Iontophoretic Treatment of Model Skin Tumors in Rats With Proflavine-Monochloride Walker Tumors where implanted on the backs of 300 g of heavy Lewis rats as model skin tumors. 7 days following the inoculation, walnut-sized tumors had developed. Two test groups were formed. In the 7-day old walnut-sized tumors, the animals of the first group were each administered an injection of 0.45 ml of a 2% proflavine-monohydrochloride solution (=9 mg) at time intervals of 6 days. The tumors developed with great acceleration and were at the time of exitus (fatal termination) the size of chicken eggs 7 days following the first injection, after a difficult course of illness. According to the pertinent literature the statistical survival time of the Walker rats, also dependent upon the number of cells inoculated, is 19 days on the average (number of cells inoculated to produce the tumors for this test: 1 million).

In the second group, likewise with 7-days-old walnut-sized tumors, three intratumoral injections were given in doses identical to those above at 6-day intervals, of which each was joined for iontophoretic applications with small-surface electrodes (30 minute per session at 0.2 to 0.3 mA/cm$^2$ tumor surface). Immediately following the first session tumor growth had stopped. The animals showed a good general well-being and a weight increase during the entire subsequent treatment. On the day of the third and last session the tumor had already diminished to half its original size. After another 14 days no tumor was visible any longer at the original tumor site. The animals survived without tumor relapse for a year and longer.

Almost identical results were obtained with use of trypflavine-hemisulfate.

The experiment results hold true for clinical application of the procedure of the experiment on human skin tumors.

The results of this experiment were confirmed by the results of another experiment:

EXAMPLE 3

Iontophoretic Treatment of Model Skin Tumors in Mice with Proflavine-Monochloride Human pancreatic tumors (seed tumors) were transplanted onto t he backs of naked, stripped mice (20 g body weight) as model skin tumors. This tumor model is therapy-resistant and cannot be altered in a positive sense by antitumor agents.

In four sessions the first group (15 mice) where subjected to intratumoral injection at approximately 3 to 5 day intervals according to the size of the tumor between 0.25 and 0.75 mg of proflavine-monohydrochloride into each mouse in the form of a diluted aqueous solution. After the injections, iontophoretic treatments were carried out over 30 minutes with the electrodes as in Example 2 (current density 0.2 to 0.3 mA/cm$^2$). Four animals died of concurrent illnesses which were not connected with the tumor ailments or with the treatment. The tumors of the other animals regressed completely and without residual damage.

In the control group likewise including 15 animals the same proflavine-monohydrochloride quantity was likewise administered in the same time intervals, identical to the treatment group, but the local iontophoreses was not administered. All of the animals died of cachexia, or wasting away, as a result of progressing tumor growth.

Almost identical results were produced by use of 4-aminoquinoline and 4-aminopyridine.

The results of the experiment hold true of clinical application of the procedure to human mucus membrane tumors.

EXAMPLE 4

Clinical Treatment with Proflavine-Monohydrochloride

W. Sch., male, aged 67 years

A multilocular recidivistic bladder carcinoma was present which had been unsuccessfully treated before within approximately the past 3 years at another facility by transurethral electroresectioning and an almost two-year application of a local continuous antitumor agent. With the constant intake, the most difficult bladder tenesmus existed with a five-minute frequency of miction (urination), yielding a raspberry colored urine and frequent coagulation discharges.

Five intravascular proflavine iontophoreses where carried out with 0.1% proflavine-monohydrochloride as bladder instillation in each case lasting for one half hour at 50 mA. Then followed a rapid stopping of the hematuria and a general recurrence of the tenesmus. One hundred ten days following the beginning of the treatment there was found macroscopically and histologically no longer any indication to suspect the presence of a tumor. Two months later there was total freedom from tumors, determined cystoscopically, and the bladder mucus membrane was totally without irritation without any hint of a relapse of a carcionma.

EXAMPLE 5

Treatment With Proflavine-Monochloride/DMSO

D. M., female, aged 77 years

Diagnosis

Characteristic infiltrating bladder carcinoma with blocking of the urine on both sides (first illness).

Preparation Used for Treatment 1 g of proflavine-monohydrochloride, 150 g DMSO. 850 ml of distilled water.

Treatment and Its Course

A total of 6 intravascular iontophoreses each of one-hour length were carried out at time intervals of 7 days with different solutions at 50 mA without anesthesia and without complications. By means of cystoscopic monitoring, on the seventh day following the beginning of the treatment already a remarkable flattening of the tumorous modifications and a shrinkage of the nodulous tumor substrate were established. On the 33d day following beginning of the treatment only a tumor remnant the size of an orange kernel still remained identifiably in the trigonum. The patient was released in good general condition after 43 days with on urological complications and without any particular bladder symptoms.

The preferred lubricant, anesthesia and prophylactic according to the invention as well as its use are explained in greater detail in the following examples.

EXAMPLE 6

5 g polidocanol (600 NW) are mixed with 95.5 g anhydrous glycerine, whereupon a viscous mixture is obtained with an electric conductivity of lower than or equal to 0.1 mS/cm.

EXAMPLE 7

10 ml of the solution obtained in Example 6 were injected by means of a syringe tipped with an olive into the urethra of a male bladder cancer patient. After about 10 minutes the analgetic action began to take effect, whereupon a positive electrode 1, as described above, was introduced, and the patient complained of no pain and there were no injuries to the urethra. The outside nonconductive shaft of the electrode was surrounded with insulation formed by a cohesive film of the medium according to the invention. Approximately 150 ml of an aqueous solution of proflavinemonohydrochloride (0.1% by weight) and dimethyl sulfoxide (15% by weight) were introduced through the electrode which was so placed. The iontophoresis was carried out for 60 minutes at 40 ma, which corresponded to a current density in the area of the bladder mucus membrane of about 0.3 mA/cm$^2$.

After the iontophoresis the therapeutic bladder instillation (proflavinemonohydrochloride, DMSO and water) was drained off, and the bladder was rinsed with distilled water.

Then 20 ml of the solution of Example 6 was injected directly into the bladder through the tubular electrode as post-treatment medium, whereupon the electrode was removed. The medium remained in the bladder until its natural discharge.

The effect of this post-treatment is expressed in a considerable lessening of the miction frequency and also in universal avoidance of bladder spasms, which otherwise would lead to a functional diminution of the bladder capacity.

The required bladder capacity for necessary further iontophoretic treatment was maintained on the basis of this treatment.

When the medium of Example 6 was not used for another patient, who had an extensively damaged bladder as a result of previous conventional treatment, then this patient complained during the iontophoresis treatment about pains in the urethra. A portion of the bladder instillation was pressed outward against the electrode lying in the urethra as a result of a bladder spasm. The further iontophoretic treatment of this patient had to be interrupted for about 4 weeks, until attenuation of the negative symptomatic (complication).

What is claimed is:

1. In the treatment of solid tumors, the improvement comprising applying to the tumor in an iontophoretic process a dissociable heterocyclic compound selected from the group consisting of aminoacridine, aminoquinoline and aminopyridine compounds in tautomeric diimine form in which the active ingredient is a cation.

2. The treatment of claim 1 in which the heterocyclic compound is present in salt form.

3. The treatment of claim 2 in which the heterocyclic compound is present as a physiologically compatible salt.

4. The treatment of claim 3 in which said physiologically compatible salt is selected from mono- or di-chloride, sulfate, lactate or acetate salts.

5. The treatment of claim 1 in which the heterocyclic compound is proflavine-monohydrochloride.

6. The treatment of claim 1 in which the heterocyclic compound is present in a mixture with dimethyl sulfoxide in aqueous solution.

7. The treatment of claim 1 in which the heterocyclic compound is in aqueous solution in a concentration of 0.05 g/l up to the limit of solubility.

8. The treatment of claim 6 in which said heterocyclic compound is present in a concentration up to 5 g/l.

9. The treatment of claim 7 in which said dimethyl sulfoxide is employed in aqueous solution in a concentration of 20 to 300 g/l.

10. The treatment of claim 7 in which the iontophoretic treatment is applied by means of a direct current, and the current density applied is not higher than 0.5 mA/cm$^2$.

11. The treatment of claim 1 in which the malignant tissue is a bladder, and the composition is introduced into the bladder through a positive tubular electrode.

12. A method of treating solid tumors comprising applying to the tumor in an iontophoretic process, a therapeutically effective amount of an aminoacridine salt in its cationic tautomeric diimine form.

13. The method of claim 12 in which the aminoacridine is proflavine-monohydrochloride.

14. A pharmaceutical composition for the treatment of solid tumors in an iontophoretic process, said composition comprising an aqueous solution of a dissociable heterocyclic compound selected from the group consisting of aminoacridine, aminoquinoline and aminopyridine compounds in their tautomeric diimine form, in which the active ingredient is a cation, in admixture with dimethylsulfoxide.

15. The composition of claim 14 in which the compound is an aminoacridine.

16. The composition of claim 15 in which the aminoacridine is proflavine-monohydrochloride.

17. A method of using a dissociable heterocyclic compound selected from the group consisting of aminoacridine, aminoquinoline and aminopyridine compounds, which are present in their tautomeric diimine form, in which the active ingredient is a cation, comprising adding said compound to an aqueous solution for the iontophoretic treatment and relapse or recidivism prophylaxis of solid tumors.

* * * * *

UNITED STATES PATENT AND TRADEMARK OFFICE
CERTIFICATE OF CORRECTION

PATENT NO. : 5,002,956

DATED : March 26, 1991

INVENTOR(S) : Karl Heinz Thiel

It is certified that error appears in the above-identified patent and that said Letters Patent is hereby corrected as shown below:

Col. 8, line 42, "derivative" should be --derivatives--;

Col. 10, line 16, "t he" should be --the--;

Col. 10, line 40, "of" should be --for--;

Col. 11, line 20, "on" should be --no--;

Signed and Sealed this

Twenty-fourth Day of November, 1992

Attest:

DOUGLAS B. COMER

*Attesting Officer*  *Acting Commissioner of Patents and Trademarks*